US012630520B2

(12) United States Patent
Wu et al.

(10) Patent No.: US 12,630,520 B2
(45) Date of Patent: May 19, 2026

(54) LEFT-HANDED BICYCLIC MORPHOLINE AND SALT THEREOF, PREPARATION METHOD THEREFOR, PHARMACEUTICAL COMPOSITION, AND USE

(71) Applicants: Institute of Materia Medica, Chinese Academy of Medical Sciences, Beijing (CN); Changchun Intellicrown Pharmaceutical Co., Ltd., Jilin (CN)

(72) Inventors: Song Wu, Beijing (CN); Hua Sun, Beijing (CN); Jinlan Zhang, Beijing (CN); Wenxuan Zhang, Beijing (CN); Zhe Wang, Beijing (CN); Qingyun Yang, Beijing (CN); Lin Jiang, Beijing (CN); Zihan Chen, Beijing (CN); Jing Shen, Beijing (CN); Jie Zhang, Beijing (CN); Chi Zhang, Beijing (CN); Zunsheng Han, Beijing (CN); Tong Qin, Beijing (CN); Yuanyuan Zhang, Beijing (CN)

(73) Assignees: Institute of Materia Medica, Chinese Academy of Medical Sciences, Beijing (CN); Changchun Intellicrown Pharmaceutical Co., Ltd., Jilin (CN)

( * ) Notice: Subject to any disclaimer, the term of this patent is extended or adjusted under 35 U.S.C. 154(b) by 911 days.

(21) Appl. No.: 17/775,402

(22) PCT Filed: Sep. 15, 2020

(86) PCT No.: PCT/CN2020/115410
§ 371 (c)(1),
(2) Date: May 9, 2022

(87) PCT Pub. No.: WO2021/103749
PCT Pub. Date: Jun. 3, 2021

(65) Prior Publication Data

US 2023/0002343 A1 Jan. 5, 2023

(30) Foreign Application Priority Data

Nov. 28, 2019 (CN) ........................ 201911190936.4

(51) Int. Cl.
*C07D 317/68* (2006.01)
*A61P 1/16* (2006.01)

(52) U.S. Cl.
CPC .............. *C07D 317/68* (2013.01); *A61P 1/16* (2018.01); *C07B 2200/07* (2013.01)

(58) Field of Classification Search
None
See application file for complete search history.

(56) References Cited

U.S. PATENT DOCUMENTS 10,751,307 B2 8/2020 Saakian

FOREIGN PATENT DOCUMENTS

| | | | | |
|---|---|---|---|---|
| CN | 1506363 A | | 6/2004 | |
| CN | 1837203 A | | 9/2006 | |
| CN | 107488162 A | * | 10/2016 | ........... C07D 317/68 |
| RU | 2545876 C2 | | 10/2014 | |

OTHER PUBLICATIONS

Nishida et al., Organic Letters (2006), 8(16), pp. 3489-3492.*
PCT International Search Report for PCT Application No. PCT/CN2020/115410 mailed Nov. 18, 2020 (5 pages, with English translation).
PCT Written Opinion for PCT Application No. PCT/CN2020/115410 mailed Nov. 18, 2020 (3 pages).
Chinese Office Action for CN Application No. 201911190936.4 mailed Apr. 8, 2022 (4 pages).
Li et al., "Inhibition of Fas/FasL mRNA Expression of TNF-α Release in Concanavalin A-Induced Liver Injury in Mice by Bicyclol," World J Gastroenterol, 2004, 10(12):1775-1779.
European Extended Search Report dated Nov. 7, 2023 for EP Application No. 20892802.8 (5 pages).
First Office Action dated Dec. 1, 2023 for RU Application No. 2022117193 (18 pages including English Translation).
First Examination Report dated Dec. 6, 2023 for AU Application No. 2020390812 (3 pages).

* cited by examiner

*Primary Examiner* — Brian J Davis
(74) *Attorney, Agent, or Firm* — Merchant & Gould P.C.

(57) ABSTRACT

The invention relates to the field of pharmaceutical chemistry, and it particularly relates to a left-handed bicyclic morpholine and a pharmaceutically acceptable salt thereof, a preparation method therefor, a pharmaceutical composition and use thereof in the preparation of medicaments for preventing and/or treating liver diseases and the like.

15 Claims, 1 Drawing Sheet

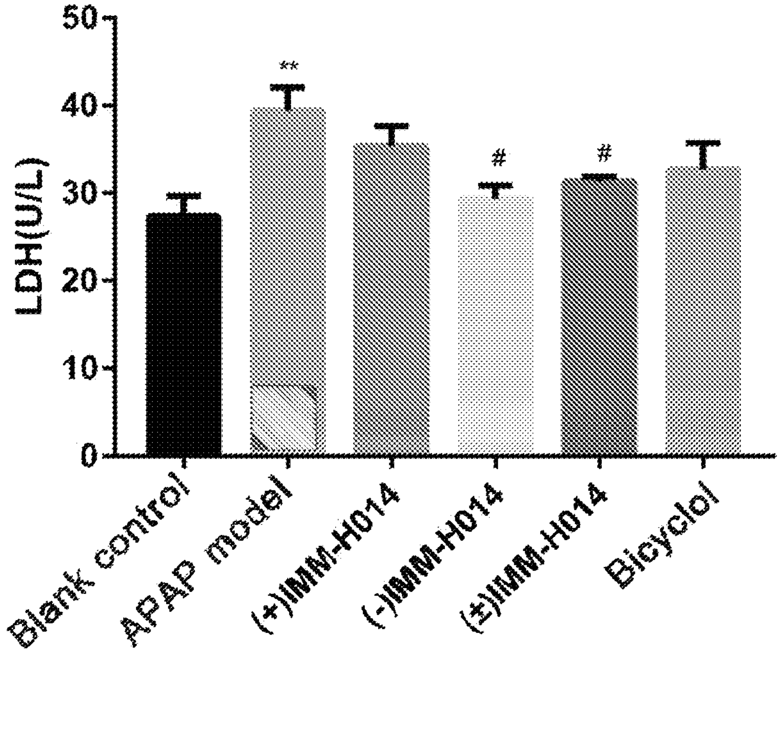
50
40
30
20
10
0
LDH(U/L)
**

Blank control
APAP model
(+)IMM-H014
(-)IMM-H014
(±)IMM-H014
Bicyclol

LEFT-HANDED BICYCLIC MORPHOLINE AND SALT THEREOF, PREPARATION METHOD THEREFOR, PHARMACEUTICAL COMPOSITION, AND USE

CROSS-REFERENCE TO RELATED APPLICATIONS

This application is a U.S. National Stage Application of PCT/CN2020/115410, filed 15 Sep. 2020, which claims priority to Serial No. 201911190936.4, filed 28 Nov. 2019, and which applications are incorporated herein by reference. To the extent appropriate, a claim of priority is made to the above disclosed applications.

TECHNICAL FIELD

The invention relates to the field of pharmaceutical chemistry, and it particularly relates to a left-handed bicyclic morpholine and a pharmaceutically acceptable salt thereof, a preparation method therefor, a pharmaceutical composition and an use thereof in the preparation of medicaments for preventing and/or treating liver diseases and the like

BACKGROUND ART

Liver diseases are a kind of worldwide diseases, and China is a large country of liver diseases. At present, in our country, there are a number of patients suffering from liver injuries and liver inflammations caused by various reasons, predominantly from viral hepatitis. Statistically, direct economic losses per year caused by chronic hepatitis (including liver cirrhosis and liver cancer caused by late chronic hepatitis) in our country reach 900 billion Renminbi. In recent years, the incidences of drug-induced liver diseases, alcoholic and non-alcoholic fatty liver diseases, and autoimmune liver diseases also exhibit a tendency of increasing year by year. Seeking for safe and effective drugs for preventing and treating liver diseases is always a research hot spot for various research institutes and pharmaceutical companies all over the world.

Bicyclol is a kind of Category 1 of Chemical Drugs for treating hepatitis in China with Chinese independent intellectual property rights which is firstly developed by Institute of Materia Medica Chinese Academy of Medical Science (MMA), and in clinic, they have the advantages of good effects in liver protection and enzyme degradation, certain activities against hepatitis virus, convenient administrations without any significant adverse reactions, and wide pharmacological activities. Research achievements relating to the Bicyclol successively win a plurality of awards, including "9$^{th}$ Five-year National Science and Technology Key Task Achievement Award (2002), Top Ten News in Chinese Pharmaceuticals Industry in 2002, First Prize of Beijing Scientific and Technological Progress (2005), Second Prize of National Scientific and Technological Progress (2007), and the like, and Bicyclol has been protected with compound invention patent rights in sixteen countries/regions, e.g., the United states, European Union, Japan, Korea and the like, and in the Taiwan region, and sold to countries like Ukraine. Since the day Bicyclol was announced to be on the market in the news conference held in Great Hall of the People in 2001.11, it has achieved huge social and economic benefits for our country.

However, Bicyclol is inferior in the biological water solubility so that it is not highly bioavailable. Researchers in Institute of Materia Medica Chinese Academy of Medical Science optimize the structure of Bicyclol, and find that the bicyclic morphine and salts thereof have good pharmacological activities and pharmacokinetic properties (Wu Song, Sun Hua, et al., Bicyclol Derivative and Preparations and Applications Thereof, 201610922563.5). On the basis of the previous findings, the researchers resolute the racemate of bicyclic morpholine, and find that the left-handed bicyclic morpholine and salts thereof have better pharmacological activities and pharmacokinetic properties in the aspects of anti-inflammation and liver protection than the racemate, and the dextro morpholine and salts thereof.

SUMMARY OF THE INVENTION

The technical problem solved by the invention is to provide a left-handed bicyclic morpholine and a pharmaceutically acceptable salt thereof, a preparation method therefor, and use thereof in the preparation of medicaments for preventing and/or treating liver diseases and the like.

In order to solve the technical problem of the invention, the invention provides the following technical solutions:

A first aspect of the technical solution according to the invention is to provide a left-handed bicyclic morpholine with a structure as shown by Compound 5, and a pharmaceutically acceptable salt thereof having a structure represented by formula (I):

5

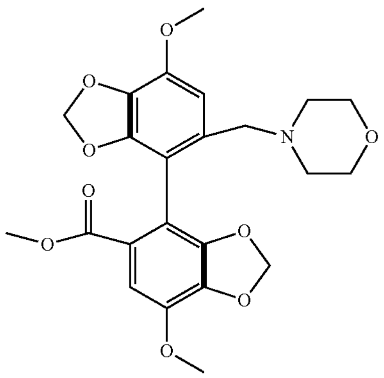

I

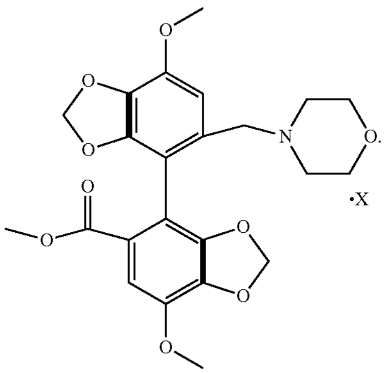

Therein, a pharmaceutically acceptable acid addition salt can be prepared from inorganic acids and organic acids. Therein, X is selected from inorganic acids and organic acids; the inorganic acids are selected from hydrofluoric acid, hydrochloric acid, hydrobromic acid, hydroiodic acid, acetic acid, sulfuric acid, and phosphoric acid; the organic acids are selected from acetic acid, trifluoroacetic acid, propionic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, quinic acid, camphoric acid, camphorsulfonic acid, aspartic acid, glutamic acid, pyroglutamic acid, L-tartaric acid, L-dibenzoyl tartaric acid, L-di-p-methylbenzoyl tartaric acid, L-diethyl tartrate, L-malic acid, L-camphoric acid, L-10-camphorsulfonic acid, R-(−)-mandelic acid, L-quinic acid, L-aspartic acid, L-glutamic acid, L-pyroglutamic acid, D-tartaric acid, D-dibenzoyl tartaric acid, D-di-p-methylbenzoyl tartaric acid, D-diethyl tartrate, D-malic acid, D-camphoric acid, D-10-camphorsulfonic acid, S-(−)-mandelic acid, D-quinic acid, D-aspartic acid, D-glutamic acid, and D-pyroglutamic acid, wherein the ratio of a free base to acid is optionally 1:1, 2:1 or 3:1. Therein, a preferred structure is shown below:

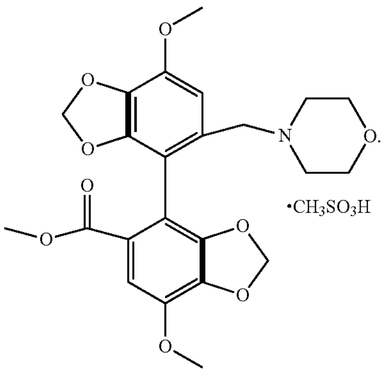

A second aspect of the technical solution according to the invention is to provide a process of preparing the left-handed bicyclic morpholine and the pharmaceutically acceptable salt thereof according to the first aspect, which is shown below:

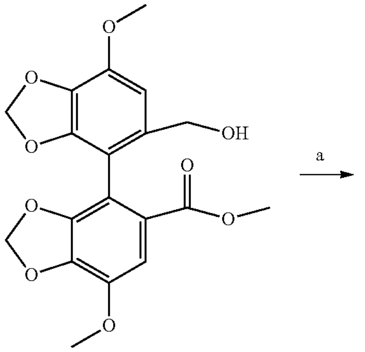

1

-continued

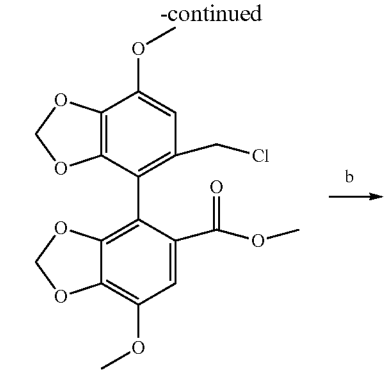

2

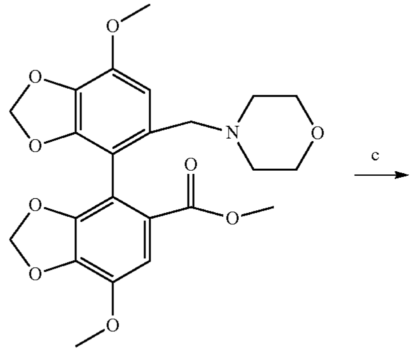

3

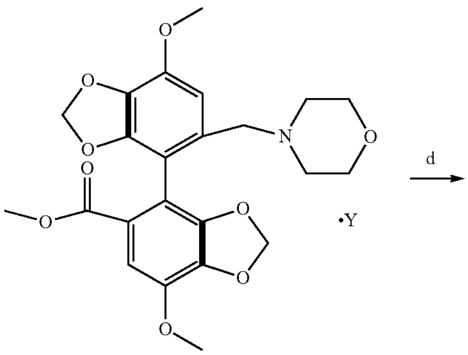

4

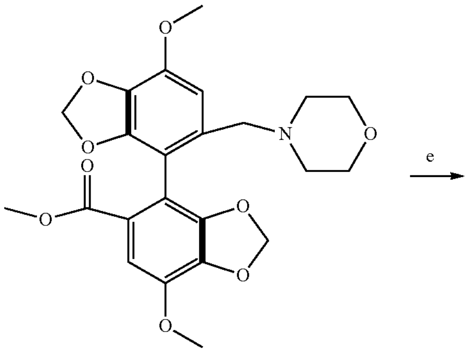

5

-continued

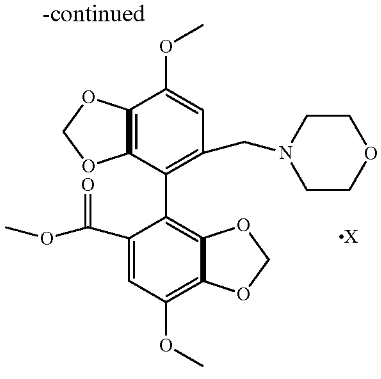

I a) chlorinating a hydroxy group of Bicyclol to obtain a compound 2; b) reacting the compound 2 with a morpholine to obtain a compound 3; c) forming a salt by reacting the compound 3 with a chiral acid Y, and performing a resolution in an organic solvent by utilizing the difference of salt solubility to obtain a salt 4, as a levo enantiomer, the levo enantiomer having an enantiomeric excess percentage (% e.e.) of more than 95.0%; wherein the chiral acid Y is selected from L-tartaric acid, L-dibenzoyl tartaric acid, L-di-p-methylbenzoyl tartartic acid, L-diethyl tartrate, L-malic acid, L-camphoric acid, L-10-camphorsulfonic acid, R-(-)-mandelic acid, L-quinic acid, L-aspartic acid, L-pyroglutamic acid, D-tartaric acid, D-dibenzoyl tartaric acid, D-di-p-methylbenzoyl tartaric acid, D-diethyl tartrate, D-malic acid, D-camphoric acid, D-10-camphorsulfonic acid, S-(-)-mandelic acid, D-quinic acid, D-aspartic acid, D-glutamic acid, D-pyroglutamic acid and derivatives of the above acids, wherein the ratio of a free base to acid is optionally 1:1, 2:1 or 3:1; the organic solvent is selected from ethyl acetate, acetone, methanol, ethanol, isopropanol and mixed solvents; d) enabling the salt 4 to be a free amine under the action of a base; e) forming a salt by reacting the free amine 5 with an acid X, to obtain the compound of formula I.

Therein, the definitions for the X are the same as the definitions in the first aspect of the technical solution according to the invention.

A third aspect of the technical solution according to the invention is to provide a pharmaceutical composition, comprising a therapeutically and/or prophylactically effective amount of the left-handed bicyclic morpholine and a pharmaceutically acceptable salt thereof according to the first aspect of the present invention, and optionally one or more pharmaceutically acceptable carriers or excipients.

The pharmaceutical composition may be prepared according to well-known methods in the art. The compound of the invention may be combined with one or more pharmaceutically acceptable solid or liquid excipients and/or adjuvants to prepare into any dosage form suitable for human or animal uses. The compound of the invention is typically present in the pharmaceutical composition thereof in an amount of from 0.1 to 95% by weight.

The compound of the invention or the pharmaceutical compositions containing the same may be administered in a unit dosage form, and the administration routes may be enteral or parenteral, such as oral administration, intravenous injection, intramuscular injection, subcutaneous injection, nasal cavities, oral mucosa, eye, lung and respiratory tract, skin, vagina, rectums and the like.

The administration dosage form may be a liquid dosage form, a solid dosage form or a semi-solid dosage form. The liquid dosage form may be a solution (including a true solution and a colloidal solution), an emulsion (including a o/w type, a w/o type and a complex emulsion), a suspension, an injection (including a water injection, a powder injection and an infusion), an eye drop, a nose drop, a lotion, and a liniment; the solid dosage form may be a tablet (including a common tablet, an enteric coated tablet, a buccal tablet, a dispersible tablet, a chewable tablet, an effervescent tablet, and an orally disintegrating tablet), a capsule (including a hard capsule, a soft capsule, and an enteric coated capsule), granules, powder, pellets, dripping pills, a suppository, a pellicle, a patch, an aerosol (powder), a spray and the like; the semisolid dosage form may be an ointment, a gel, a paste, and the like.

The compound of the invention may be formulated into a common formulation, also into a sustained release formulation, a controlled release formulation, a targeting formulation and various microparticle administration systems.

In order to prepare the compound of the invention into a tablet, a wide variety of excipients known in the art may be used, including diluents, binders, wetting agents, disintegrants, lubricants, and cosolvents. The diluents may be starch, dextrin, sucrose, glucose, lactose, mannitol, sorbitol, xylitol, microcrystalline cellulose, calcium sulfate, calcium hydrophosphate, calcium carbonate and the like; the wetting agents may be water, ethanol, isopropanol and the like; the binders may be a starch slurry, dextrin, syrups, bee honey, a glucose solution, microcrystalline celluloses, an acacia slurry, a gelatin slurry, sodium carboxymethyl cellulose, methylcellulose, hydroxypropylmethyl cellulose, ethyl cellulose, acrylic resin, Carbomer, polyvinylpyrrolidone, polyethylene glycol and the like; the disintegrants may be dry starch, microcrystalline cellulose, lowly substituted hydroxypropyl cellulose, crosslinked polyvinylpyrrolidone, crosslinked sodium carboxymethylcellulose, sodium carboxymethyl starch, sodium bicarbonate and citric acid, polyoxyethylene sorbitol fatty acid ester, sodium dodecyl sulfate and the like; the lubricants and the cosolvents may be talc powder, silica, stearate, tartaric acid, liquid paraffin, and polyethylene glycol.

The tablets may be further prepared into coated tablets, such as sugar coated tablets, film coated tablets, enteric coated tablets, or two-layered and multi-layered tablets.

In order to prepare an administration unit into capsules, the effective ingredient, the compound of the invention, is mixed with a diluent and a cosolvent, and the resultant mixture is directly placed in hard capsules or soft capsules. Also, the effective ingredient, the compound of the invention, is mixed with a diluent, a binder and a disintegrant to prepare granules or pellets, and then placed in hard capsules or soft capsules. Various species of the diluent, the binder, the wetting agent, the disintegrant, and the cosolvent for preparing the tablets of the compound of the invention can be also used to prepare the capsules of the compound of the invention.

In order to prepare the compound of the invention into an injection, water, ethanol, isopropanol, propylene glycol or their mixtures can be used as the solvent, and appropriate amounts of solubilizers, cosolvents, pH regulators and osmotic pressure regulators, commonly used in the art, may be added; the solubilizers or the cosolvents may be Poloxamer, lecithin, hydroxypropyl-β-cyclodextrin and the like; the pH regulators may be phosphate, acetate, hydrochloric acid, sodium hydroxide and the like; the osmotic pressure regulators may be sodium chloride, mannitol, glucose, phosphate, acetate, and the like. If a lyophilized powder for injection is prepared, mannitol and glucose may also be added as a proppant. Additionally, colorants, preservatives, flavors, or other additives may be also added to the pharmaceutical formulation, if desired.

In order to realize administration purposes and enhance therapeutic effects, the drugs or pharmaceutical compositions of the invention may be administered by any known administration methods.

The administration dose of the pharmaceutical compositions comprising the compound of the invention may vary in a broad scope depending on natures and severities of diseases to be prevented or treated, individual conditions of patients or animals, administration routes and dosage forms. Generally, a suitable range of the daily dose for the compounds of the invention is 0.001-5 mg/Kg body weight. The above dose may be administered in one dose unit or by dividing it into several dose units, depending on clinical experiences of physicians and administration regimens including uses of other therapeutic means.

The compounds or compositions of the invention may be administered alone or in combination with other therapeutic or symptomatic drugs. When the compound of the invention synergistically has effects with other therapeutic agents, its dose should be adjusted according to actual situations.

A fourth aspect of the technical solution according to the invention is to provide use of the left-handed bicyclic morpholine and the pharmaceutically acceptable salt thereof according to the first aspect, and the pharmaceutical composition according to the third aspect in the preparation of medicaments for preventing and/or treating liver-related diseases. Therein, the liver-related diseases are selected from liver injury-related diseases and hepatitis-related diseases, particularly including hepatitis A, hepatitis B, hepatitis C, drug-induced liver diseases, alcoholic liver diseases, non-alcoholic liver diseases, autoimmune liver diseases, hepatic fibrosis induced by liver disease progression, liver cirrhosis, and liver failures.

Beneficial Technical Effects of the Invention

The left-handed bicyclic morpholine and the pharmaceutically acceptable salt thereof in the invention exhibit better pharmacological activities than the dextro enantiomer and the racemate in various liver injury animal models, and there is a significant statistical difference ($P<0.05$). Besides, the left-handed bicyclic morpholine and the pharmaceutically acceptable salt thereof have better pharmacokinetic properties than the dextro enantiomer and the racemate.

BRIEF DESCRIPTION OF THE DRAWING

The FIGURE shows the reducing effects of IMM-H014 enantiomers on the LDH level increase of a cellular culture supernatant caused by 4-acetamidophenol (n=3-4). ** $P<0.01$, in comparison to a blank control group; #$P<0.05$, in comparison to a model group.

BEST MODES FOR CARRYING OUT THE INVENTION

The invention provides a left-handed bicyclic morpholine and a pharmaceutically acceptable salt thereof for treating liver diseases, a preparation method therefor, a pharmaceutical composition and use thereof. The following examples are listed to further illustrate the invention, but not limit the invention in any way. It will be understood by those skilled in the art that various changes and modifications may be made directed to the invention without departing from the spirit and scope thereof.

The nuclear magnetic resonance spectra of the left-handed bicyclic morpholine and salt thereof provided by the invention are measured by using a Varain Mercury-500 nuclear magnetic resonance meter, with a TMS as an internal standard, and the mass spectra are measured by using a ZAB-2F mass spectrometer.

Example 1 Preparation of a Levo (−)IMM-H014

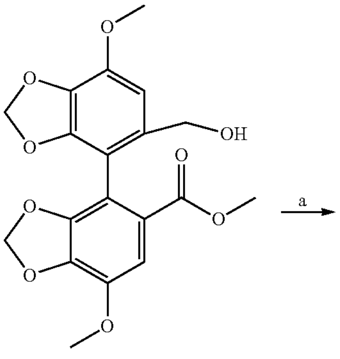

1

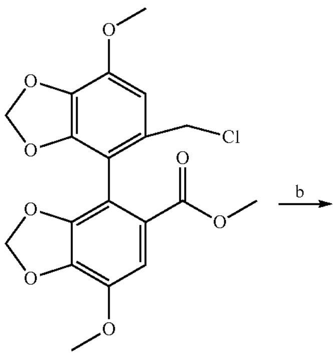

2

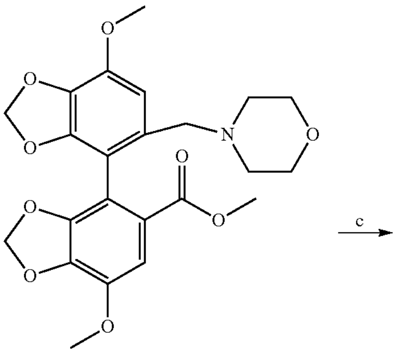

3

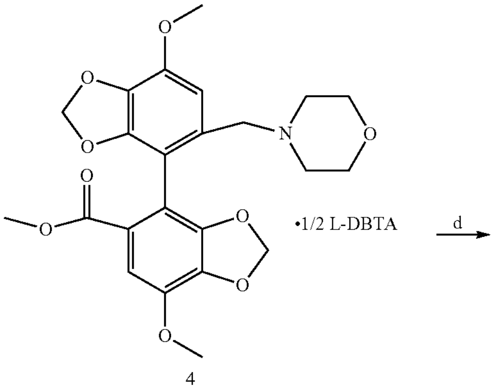

4

-continued

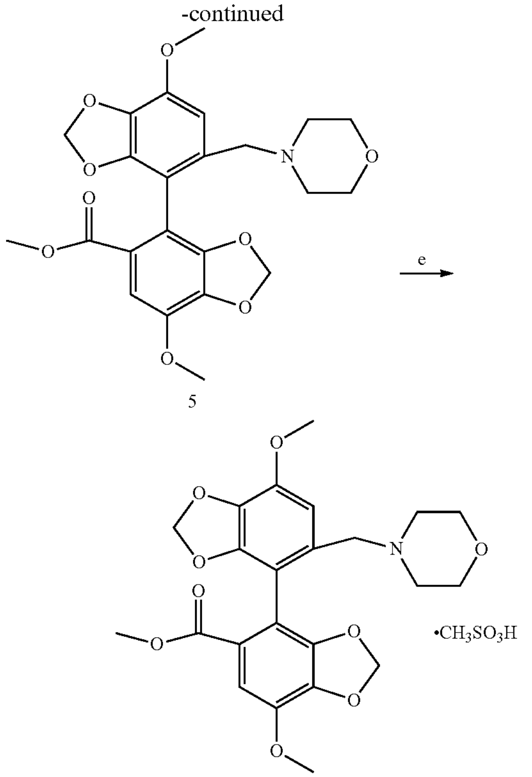

5

(-)IMM-H014 a. $SOCl_2$/DMF; b. TEA/$CH_2Cl_2$ or $CH_3COCH_3$; c. L-DBTA/EA; d. $NaHCO_3$/$H_2O$/EA; e. $CH_3SO_3H$/EA.

Compound 1 (i.e. Bicyclol, 5.1 g, 13.1 mmol) was placed in a 100 ml three-necked flask with a magnetic stirrer and a thermometer which was added with 50 ml of dry DMF, and the solids were completely dissolved. After the reaction system was cooled to 0° C. in an ice bath, $SOCl_2$ (4.5 ml, 61.8 mmol) was slowly added dropwise whilst the temperature of the system was controlled not to exceed 5° C. After the dropwise addition, the reaction was continued in an ice bath for 30 min until TLC showed that the raw materials were completely reacted. The reaction system was poured into about 100 g of crushed ice and sufficiently stirred to precipitate a large quantity of white solids which were filtered, and the filter cake was washed with small quantities of distilled water and ethers and dried by draining. The product was naturally dried by air and weighed to totally produce 4.9 g of white solids (compound 2), a yield: 91.7%.

Morpholine (1.28 g, 14.7 mmol) was placed in a 50 ml round-bottom flask which was added with 25 ml of acetone and 2.2 ml of triethylamine, and with stirring at room temperature, compound 2 (2.76 g, 6.8 mmol) was added thereto. The mixture was reacted at room temperature for 5 h and it was kept still overnight. TLC showed that the raw materials were completely reacted, and pink insoluble solids were produced in the system. With filtrations, the filtration liquid was distilled under reduced pressure to remove the solvent therein. The resultant yellow oil was separated by a vacuum column (petroleum ether:ethyl acetate=2:1), and the product components were collected, to totally produce 3.1 g of colorless oil (compound 3), a yield: 92.3%. MS-FAB $[M+H]^+$=460.1.

Compound 3 (3.0 g, 6.54 mmol) was weighed and dissolved in 45 ml of ethyl acetate, and L-dibenzoyltartaric acid (L-DBTA, 1.2 g, 3.27 mmol) was added thereto. At room temperature, the mixture was stirred to precipitate white solids, and after 30 min, it was filtered to collect the solids that were further dried at 60° C. for 1 hour and then weighed, to totally obtain 1.25 g of white solids (left-handed bicyclic morpholine:L-dibenzoyl tartaric acid=2:1), a yield: 56.8%. With chiral HPLC analyses, the enantiomeric excess percentage (% e.e.) of intermediate 4 was 98.0%, $[\alpha]_{25}$=−130.4 ($CH_2Cl_2$).

Intermediate 4 (1.25 g) was dispersed with 25 mL of ethyl acetate and washed twice with 25 mL of a saturated sodium bicarbonate solution, and the organic phase was dried over anhydrous sodium sulfate, filtered, and concentrated to produce colorless oil. The oil was dissolved in 10 ml of ethyl acetate and 120 μL of methanesulfonic acid was added thereto. Crystallization was performed at room temperature with stirring. With filtrations, the resultant solids were recrystallized with 10 ml of methanol, to produce 0.7 g of (−)IMM-H014, being white solids, HPLC purity >98.0%, [α]25=−65.6 ($CH_2Cl_2$). $^1$H NMR (500 MHz, Chloroform-d) δ 7.45 (s, 1H), 7.38 (s, 1H), 6.14 (s, 1H), 6.02 (s, 1H), 5.96 (d, J=8.9 Hz, 2H), 4.37 (dd, J=13.3, 4.0 Hz, 1H), 4.16 (t, J=12.0 Hz, 1H), 4.05 (d, J=19.7 Hz, 8H), 3.96-3.81 (m, 3H), 3.76 (s, 3H), 3.57 (d, J=11.8 Hz, 1H), 3.41 (d, J=12.5 Hz, 1H), 2.91 (s, 3H), 2.79-2.68 (m, 1H), 2.50 (d, J=11.3 Hz, 1H).

Comparative Example 1 Preparation of a Dextro Enantiomer (+)IMM-H014

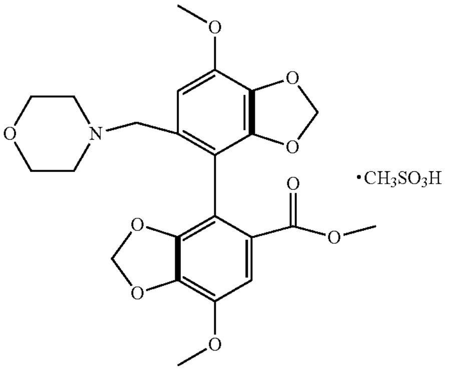

(+) IMM-H014

Compound 3 (3.0 g, 6.54 mmol) was additionally taken and dissolved in 45 ml of ethyl acetate and D-dibenzoyl tartaric acid (1.2 g, 3.27 mmol) was added thereto. The mixture was stirred at room temperature to precipitate white solids, and after 30 minutes, the solids were collected, dried at 60° C. for 1 h, and weighed to produce 1.2 g of white solids (dextro bicyclic morphine:D-dibenzoyl tartaric acid=2:1), a yield: 54.5%. With chiral HPLC analyses, the enantiomeric excess percentage (% e.e.) of intermediate 4 was 97.3%, [α]25=+133.2 ($CH_2Cl_2$). The intermediate (1.2 g) was dispersed with 25 mL of ethyl acetate and washed twice with 25 mL of a saturated sodium bicarbonate solution, and the organic phase was dried over anhydrous sodium sulfate, filtered, and concentrated to obtain colorless oil. The oil was dissolved in 10 ml of ethyl acetate and 120 μL of methanesulfonic acid was added thereto. Crystallization was performed at room temperature with stirring. With filtrations, the resultant solids were recrystallized with 10 mL of methanol to obtain 0.6 g of (+)IMM-H014, being white solids, HPLC purity >98.0%, $[\alpha]_{25}$=−78.2 ($CH_2Cl_2$). $^1H$ NMR (500 MHz, Chloroform-d) δ 7.45 (s, 1H), 7.38 (s, 1H), 6.14 (s, 1H), 6.02 (s, 1H), 5.96 (d, J=8.9 Hz, 2H), 4.37 (dd, J=13.3, 4.0 Hz, 1H), 4.16 (t, J=12.0 Hz, 1H), 4.05 (d, J=19.7 Hz, 8H), 3.96-3.81 (m, 3H), 3.76 (s, 3H), 3.57 (d, J=11.8 Hz, 1H), 3.41 (d, J=12.5 Hz, 1H), 2.91 (s, 3H), 2.79-2.68 (m, 1H), 2.50 (d, J=11.3 Hz, 1H).

Pharmacological Experiments

Experimental Example 1 Effects of IMM-H014 Optical Enantiomers on Phytohemagglutinin (ConA)-Induced Acute Immune Liver Injuries 1. Method for Establishment of a ConA-Induced Mouse Acute Immune Liver Injury Model and Method of Administration SPF-grade male ICR mice (20-22 g), after acclimatization, were randomly divided into 5 groups: a blank control group, a ConA-induced model group, a 200 mg/kg (+)IMM-H014 group, a 200 mg/kg (−)IMM-H014 group, and a 200 mg/kg (±)IMM-H014 group, 10 mice in each group. Each administration group was intragastrically administrated once a day, and it was totally administrated three times. The blank control group and the model group were intragastrically administrated with the same dose of physiological saline. At 2 hours after the last administration, the mice in each group except the blank control group, were injected once with 20 mg/kg ConA in the tail vein, and each administration dose was 10 ml/kg. The mice were in fasting but not in water deprivation for 16 h and then the animals waited for further treatment.

2. Determination of Biochemical Indexes

The mice were decapitated and blood was taken, and the blood samples were kept still at room temperature for 2 h and centrifuged at 4000 rpm for 10 min, to separate the serum. The ALT, AST and LDH contents in the serum were detected with a full-automatic biochemical analyzer.

3. Statistical Analysis

The data each were presented as a number mean±standard deviation ($\bar{x}$±SD). The comparisons between the groups were performed by a t-test and the P<0.05 indicated that there was a significant difference.

4. Experimental Results 4.1 Effects of IMM-H014 Enantiomers on ConA-Induced Increases of the Biomarker ALT of Serum Liver Injuries The serum ALT level exhibits direct and positive correlations with the degree of liver injuries, and it is a recognized serum biomarker for liver injuries. The results in Table 1 showed that 20 mg/kg ConA would result in significant liver injuries in mice, and the serum ALT levels significantly increased as compared to the blank control group (P<0.001). Both the (+)IMM-H014 and the (−)IMM-H014 could significantly reduce the ConA-induced increases of the serum ALT (P<0.001). The reduction percent of the ALT by IMM-H014 enantiomers was 95.3% and 97.3% respectively, and the ALT contents were reduced to the level of the blank control group. Both the (+)IMM-H014 and (−)IMM-H014 showed significant protective effects on ConA-induced immune liver injuries, and the activity of the (−)IMM-H014 was slightly superior to that of the (+)IMM-H014. As compared to the (±)IMM-H014 at the same dose, the reducing effects of the (+)IMM-H014 and (−) IMM-H014 on the ConA-induced increases of mouse serum ALT levels were superior to that of the (±)IMM-H014 (which also showed remarkable efficacy, and the reduction percent of the ALT was 88.6%), wherein the reducing effects of the (−)IMM-H014 on the ALT had a statistic difference (P<0.05) as compared to that of the (±)IMM-H014.

TABLE 1

Reducing effects of IMM-H014 enantiomers on ConA-induced increases of mouse serum ALT (n = 10)

| Group | Doses (mg/kg) | ALT (U/L) | ALT reduction percent (%) |
|---|---|---|---|
| Blank control group | — | 39.5 ± 9.6 | — |
| ConA-induced model group | — | 937.5 ± 529.2*** | — |
| (+)IMM-H014 | 200 | 44.4 ± 29.1$^{\#\#\#}$ | 95.3 |
| (−)IMM-H014 | 200 | 25.6 ± 17.4$^{\#\#\#\&}$ | 97.3 |
| (±)IMM-H014 | 200 | 107.0 ± 108.7$^{\#\#\#}$ | 88.6 |

***P < 0.001, in comparison to the blank control group;
$^{\#\#\#}$P < 0.001, in comparison to the model group;
$^{\&}$P < 0.05, in comparison to the (±)IMM-H014 group.

4.2 Effects of IMM-H014 Enantiomers on ConA-Induced Increases of the Biomarker AST of Serum Liver Injuries The increase of the serum AST level is also one important marker for hepatocyte injuries, particularly hepatocyte mitochondrial injuries, and when the mitochondria is injured, the serum AST level is remarkably increased, to reflect the severity of hepatocyte. The results were shown in Table 2, 20 mg/kg ConA caused the mouse hepatocyte mitochondria to be significantly injured, and the serum AST level was significantly increased as compared to the blank control group (P<0.001). All the (+)IMM-H014, (−)IMM-H014 and (±)IMM-H014 were able to reduce the level of the ConA-induced increases of serum AST. In comparison to the model group, the AST reduction percent by (+)IMM-H014, (−)IMM-H014 and (±)IMM-H014 was 44.8%, 72.9% and 22.2% respectively, wherein the (−)IMM-H014 group had a statistic difference (P<0.01) as compared to the model group. The activities of the (+)IMM-H014 and (−)IMM-H014 for reducing the AST were superior to that of the (±)IMM-H014, and the activity of the (−)IMM-H014 was optimal and had a statistic difference (P<0.05) as compared to the (±)IMM-H014 group at the same dose.

TABLE 2

Reducing effects of IMM-H014 enantiomers on ConA-induced increases of mouse serum AST (n = 10)

| Group | Dose (mg/kg) | AST (U/L) | AST reduction percent (%) |
|---|---|---|---|
| Blank control group | — | 72.0 ± 24.5 | — |
| ConA-induced model group | — | 931.7 ± 489.2*** | — |
| (+)IMM-H014 | 200 | 514.3 ± 310.7 | 44.8 |
| (−)IMM-H014 | 200 | 252.9 ± 233.5$^{\#\#\&}$ | 72.9 |
| (±)IMM-H014 | 200 | 725.0 ± 417.3 | 22.2 |

***P < 0.001, in comparison to the blank control group;
$^{\#\#}$P < 0.01, in comparison to the model group;
$^{\&}$P < 0.05, in comparison to the (±) IMM-H014 group.

4.3 Effects of IMM-H014 Enantiomers on ConA-Induced Increases of Serum LDH

When the liver is injured, the serum LDH level could also reflect situations and degrees of hepatocyte injuries. The results were shown in Table 3. The administration of 20 mg/kg ConA by tail vein injection caused severe hepatocyte injuries, and the serum LDH level was significantly increased as compared to the blank control group (P<0.001). The (−)IMM-H014 could significantly reduce the level of the ConA-induced serum LDH increase, and the reduction percent of the LDH was up to 54.4%, which had a statistical difference (P<0.01) as compared to the model group. The (+)IMM-H014 also had the reducing effects on the increase of serum LDH, and the reduction percent was 27.6%, which did not have a statistical difference as compared to the model group. The (±)IMM-H014, at the present dose, only had weak reducing effects on the LDH increase, and the reduction percent was 6.4%. In the aspect of reducing the LDH level, the activity of the (−)IMM-H014 was still superior to those of the (+)IMM-H014 and (±)IMM-H014, and there was a statistical difference (P<0.05) between (−)IMM-H014 and (±)IMM-H014 at the same dose.

TABLE 3

Reducing effects of IMM-H014 enantiomers on Con-A induced increases of mouse serum LDH (n = 10)

| Group | Dose (mg/kg) | LDH (U/L) | LDH reduction percent (%) |
|---|---|---|---|
| Blank control group | — | 1158.5 ± 289.7 | — |
| ConA-induced model group | — | 3702.5 ± 1221.0*** | — |
| (+)IMM-H014 | 200 | 2680.0 ± 1190.8 | 27.6 |
| (−)IMM-H014 | 200 | 1690.0 ± 929.3##& | 54.4 |
| (±)IMM-H014 | 200 | 3466.7 ± 1772.4 | 6.4 |

***P < 0.001, in comparison to the blank control group;
P < 0.01, in comparison to the model group;
&P < 0.05, in comparison to the (±) IMM-H014 group.

Experimental Example 2 Effects of IMM-H014 Optical Enantiomers on Ethionine-Induced Non-Alcoholic Fatty Liver Diseases 1. Method for Establishment of an Ethionine-Induced Mouse Non-Alcoholic Fatty Liver Model and Method of Administration SPF-grade male ICR mice (20-22 g), after acclimatization, were randomly divided into 5 groups: a blank control group, an ethionine-induced model group, a 200 mg/kg (+)IMM-H014 group, a 200 mg/kg (−)IMM-H014 group, and a 200 mg/kg (±)IMM-H014 group, 5 mice in each group. Three days before the establishment of the models, each administration group was intragastrically administrated once per day, and it was totally administrated three times. The animals in the blank control group and the model group were intragastrically administrated with the same dose of physiological saline. Each administration dose was 10 mL/kg. One hour after the last administration, the mice in each group were intragastrically administrated with 250 mg/kg ethionine once. The administration dose was 20 ml/kg. The mice were in fasting but not in water deprivation for 24 h and then the animals waited for further treatment.

2. Determinations of the Contents of Triglyceride and Cholesterol in Liver Tissues The mice were subjected to thoracotomy to take out the livers which were washed with physiological saline at 4° C. A part of the liver tissues were prepared into a 10% liver tissue homogenate with a lysate and an electric homogenizer, wherein one part was measured according to the measurement methods of a triglyceride kit and a cholesterol kit to determine the triglyceride and cholesterol therein, and the other part was measured with a BCA protein quantification kit to determine the content of proteins therein. The triglyceride and cholesterol in the liver tissues were subjected to protein corrections.

3. Statistical Analysis

By adopting SPSS software, the data each were presented as a number mean±standard deviation ($\bar{x}$±SD). The comparisons between the groups were performed by a t-test and the P<0.05 indicated that there was a significant difference.

4. Experimental Results 4.1 Effects of IMM-H014 Enantiomers on Ethionine-Induced Increases of Mouse Liver Tissue Cholesterol (TC) Contents The ethionine, by interfering metabolism of methionine to further influence the synthesis of apolipoprotein, could result in that the cholesterol and triglyceride etc. synthesized in hepatocytes could not be transported into blood, which causes accumulations of hepatocyte lipids, and thus, a drug-induced non-alcoholic fatty liver model is formed. The results were shown in Table 4, 250 mg/kg ethionine could induce a significant increase (P<0.05) of the cholesterol content in liver tissues as compared to the blank control group. Both the (+)IMM-H014 and (−) IMM-H014 could reduce the ethionine-induced accumulations of liver tissue TC, and the TC reduction percent by IMM-H014 enantiomers (i.e. (+)IMM-H014 and (−)IMM-H014) was 27.2% and 32.4% respectively, wherein the (−)IMM-H014 group had a statistical difference (P<0.05) as compared to the model group. The (±)IMM-H014 also had significant inhibitory effects on the ethionine-induced liver tissue TC increase, and it had a statistical difference (P<0.05) as compared to the model group. The activity of the (−)IMM-H014 was slightly superior to that of the (±)IMM-H014.

TABLE 4

Reducing effects of IMM-H014 enantiomers on ethionine-induced mouse liver tissue TC accumulations (n = 10)

| Group | Dose (mg/kg) | TC (mmol/gprot) | TC reduction percent (%) |
|---|---|---|---|
| Blank control group | — | 0.060 ± 0.014 | — |
| ConA-induced model group | — | 0.089 ± 0.019* | — |
| (+)IMM-H014 | 200 | 0.065 ± 0.022 | 27.2 |
| (−)IMM-H014 | 200 | 0.061 ± 0.013# | 32.4 |
| (±)IMM-H014 | 200 | 0.063 ± 0.013# | 30.0 |

*P < 0.05, in comparison to the blank control group;
#P < 0.05, in comparison to the model group.

4.2 Effects of IMM-H014 Enantiomers on Ethionine-Induced Increases of the Mouse Liver Tissue Triglyceride (TG) Contents The results were shown in Table 5. 250 mg/kg ethionine induced a significant increase (P<0.05) of the TG content in the liver tissues as compared to that of the blank control group, to exhibit symptoms of non-alcoholic fatty livers. The (−) IMM-H014 could significantly reduce the ethionine-induced liver tissue TG accumulations, and the TG reduction percent was 39.0%, which had a statistical (P<0.05) difference as compared to the model group. The (+)IMM-H014 exhibited weak reducing effects on the ethionine-induced liver tissue TG increase, only with a percent reduction ratio of 7.1%.

TABLE 5

Reducing effects of IMM-H014 enantiomers on ethionine-induced liver tissue TG accumulations (n = 10)

| Group | Dose (mg/kg) | TG (mmol/gprot) | Percent TG reduction (%) |
|---|---|---|---|
| Blank control group | — | 0.152 ± 0.0023 | — |
| ConA-induced model group | — | 0.253 ± 0.078* | — |

TABLE 5-continued

Reducing effects of IMM-H014 enantiomers on ethionine-induced liver tissue TG accumulations (n = 10)

| Group | Dose (mg/kg) | TG (mmol/gprot) | Percent TG reduction (%) |
|---|---|---|---|
| (+)IMM-H014 | 200 | 0.235 ± 0.070 | 7.1 |
| (−)IMM-H014 | 200 | 0.154 ± 0.040# | 39.0 |
| (±)IMM-H014 | 200 | 0.110 ± 0.005## | 56.6 |

*P < 0.05, in comparison to the blank control group;
#P < 0.05,
P < 0.01, in comparison to the model group

Experimental Example 3 Effects of IMM-H014 Optical Enantiomers on 4-Acetamidophenol-Induced Hepatocyte Injuries 1. Cell Culture Human liver cancer HepG2 cell well retained the characteristics of normal human hepatocytes, and they were grown in a DMEM medium containing 10% of fetal calf cerium (containing 100 U/mL of penicillin and 100 μg/mL of streptomycin) at the culturing conditions: 37° C., 5% of $CO_2$ and a saturated humidity. A solution containing 0.25% of trypsin and 0.02% of EDTA was used for digestions and passages.

2. Protective Effects of IMM-H014 Enantiomers on 4-Acetamidophenol-Induced In Vitro Hepatocyte Injuries A MTT method was adopted. The HepG2 cells were inoculated in a 96-well cell culture plate, and after 24 hour cultures, the (+)IMM-H014, the (−)IMM-H014 and the (±)IMM-H014 were added in a non-toxic concentration whilst the 4-acetamidophenol (APAP, a final concentration of 8 mM) was added thereto. A Bicyclol positive control group, a solvent control group and a model group were set for the experiment. The culture was continued for 24 h. 100 μL of the culture solution was taken and centrifuged, and a full-automatic biochemical analyzer in a LDH detection kit was utilized to detect the LDH level therein. The remaining culture solution was discarded, and to each well, 100 μL of a MTT (0.5 mg/mL) solution was added to continue the culture for 4 hours. The MTT solution was discarded, and to each well, 150 μL of DMSO was added. The mixture was oscillated by a mixing oscillator, and the absorbance value was measured at a wavelength of 570 nm in a microplate reader. Cell survival rate (%)=(OD mean of administration group/OD mean of solvent control group)×100%.

3. Statistical Analysis

The data were presented as a number mean±standard deviation ($\bar{x}$±SD). The comparisons between groups were performed by a t-test and the P<0.05 indicated that there was a significant difference.

4. Experimental Results

10 μM of the (+)IMM-H014, 10 μM of the (−)IMM-H014 and 10 μM of the (±) IMM-H014 acted on HepG2 cells for 48 h, and they were not significantly toxic to the cells, each with a cell survival rate of 90%. The concentration was utilized to investigate the protective effects on APAP injured hepatocytes. The results were shown in Table 6, 8 mM of the APAP could significantly injure the HepG2 cells, and the cell survival rate was only 38.33% (P<0.001) as compared to the blank control group. The (+)IMM-H014, (−)IMM-H014 and (±)IMM-H014 at a dose of 10 μM each had significant protective effects on APAP-induced in vitro human hepatocyte injures (P<0.05, P<0.001, P<0.01), and the percent increases of cell survival were 41.4%, 74.8% and 32.1%, respectively. The activity of the (−)IMM-H014 was relatively optimal, and it had a statistical difference as compared to the (±) IMM-H014 group at the same dose (P<0.05). Bicyclol could also significantly improve APAP-induced hepatocyte injuries (P<0.05).

TABLE 6

Effects of IMM-H014 enantiomers on 4-acetamidophenol-induced reductions of hepatocyte survival rates (n = 3-4)

| Group | Concentrations (μM) | OD Mean ± SD | Survival rates (%) | Cell survival rate increase (%) |
|---|---|---|---|---|
| Blank control group | — | 0.845 ± 0.037 | 100.00 | — |
| APAP-induced model group | — | 0.343 ± 0.029*** | 38.33 | — |
| (+)IMM-H014 | 10 | 0.489 ± 0.098# | 54.58 | 42.4 |
| (−)IMM-H014 | 10 | 0.600 ± 0.054###& | 67.01 | 74.8 |
| (±)IMM-H014 | 10 | 0.453 ± 0.032## | 50.63 | 32.1 |
| Bicyclol | 10 | 0.454 ± 0.092# | 50.67 | 32.2 |

***P < 0.001, in comparison to the blank control group;
#P < 0.05,
P < 0.01,
P < 0.001, in comparison to the model group;
&P < 0.05, in comparison to the (±)IMM-H014 group.

LDH (lactic dehydrogenase) is one important enzyme for cellular energy metabolisms. When cells die, the cytomembrane is broken and the LDH is released from the cytoplasm, and the LDH level is proportional to the degree of cell injuries. The results were shown in The FIGURE, the 8 mM APAP acted on HepG2 cells for 24 h, and the LDH level in the cell culture supernatant was significantly increased as compared to that of the blank control group (P<0.01), to further indicate significant hepatocyte injuries. The (+) IMM-H014, (−) IMM-H014 and (±) IMM-H014 at a dose of 10 uM each could reduce the LDH levels, wherein the LDH levels of the (−) IMM-H014 and (±) IMM-H014 had statistical differences (P<0.05, P<0.05) as compared to that of the model group, and the reducing effects of the (−) IMM-H014 group were slightly superior to those of the (±) IMM-H014 group at the same dose.

Experimental Example 4 Effects of IMM-H014 Optical Enantiomers on Carbon Tetrachloride-Induced Hepatocyte Injuries 1. Cell Culture Human liver cancer HepG2 cells well retained the characteristics of normal human hepatocytes, and they were grown in a DMEM medium containing 10% of fetal calf cerium (containing 100 U/mL of penicillin and 100 μg/mL of streptomycin) at the culturing conditions: 37° C., 5% of $CO_2$ and a saturated humidity. A solution containing 0.25% of trypsin and 0.02% of EDTA was used for digestions and passages.

2. Protective Effects of IMM-H014 Enantiomers on Carbon Tetrachloride-Induced In Vitro Hepatocyte Injuries A MTT method was adopted. The HepG2 cells were inoculated in a 96-well cell culture plate, and after 24 hour cultures, the (+)IMM-H014, the (−)IMM-H014 and the (±)IMM-H014 were added in a non-toxic concentration whilst the carbon tetrachloride ($CCl_4$, a final concentration of 0.6%) was added thereto. A Bicyclol positive control group, a solvent control group and a model group were set for the experiment. They acted on the cells continuously for 24 h. The culture solution was discarded, and to each well, 100 μL of a MTT (0.5 mg/mL) solution was added to culture for 4 hours. The MTT solution was discarded, and to each well, 150 μL of DMSO was added. The mixture was oscillated by a mixing oscillator, and the absorbance value was measured at a wavelength of 570 nm in a microplate reader. Cell survival rate (%)=(OD mean of administration group/OD mean of solvent control group)×100%.

3. Statistical Analysis

The data were presented as a number mean±standard deviation ($\bar{x}$±SD). The comparisons between groups were performed by a t-test and the P<0.05 indicated that there was a significant difference.

4. Experimental Results

10 μM of the (+)IMM-H014, 10 μM of the (−)IMM-H014 and 10 μM of the (±) IMM-H014 acted on HepG2 cells for 48 h, and they were not significantly toxic to the cells, each with a cell survival rate of 90%. The concentration was utilized to investigate the protective effects on $CCl_4$ injured hepatocytes. The results were shown in Table 7, the 0.6% $CCl_4$ could significantly injure the HepG2 cells, and the cell survival rate was 77.50% (P<0.001) as compared to the blank control group. The (+)IMM-H014, (−)IMM-H014 and (±)IMM-H014 at a dose of 10 μM each had significant improving effects on the $CCl_4$-induced in vitro human hepatocyte injures (P<0.05, P<0.01, P<0.01), and the percent increases of cell survival were 12.59%, 34.66% and 18.74%, respectively. As compared to the (±)IMM-H014 at the same dose, the (−)IMM-H014 had a better protective activity on the $CCl_4$-induced hepatocyte injures. Bicyclol could also significantly improve APAP-induced hepatocyte injuries.

TABLE 7

Effects of IMM-H014 enantiomers on reductions of hepatocyte survival rates caused by 4-acetamidophenol (n = 3-4)

| Group | Concentrations (μM) | OD Mean ± SD | Survival rates (%) | Cell survival rate increase (%) |
|---|---|---|---|---|
| Blank control group | — | 0.915 ± 0.128 | 100.00 | — |
| APAP-induced model group | — | 0 709 ± 40.043** | 77.50 | — |
| (+)IMM-H014 | 10 | 0.799 ± 0.014# | 87.32 | 12.59 |
| (−)IMM-H014 | 10 | 0.956 ± 10.120## | 104.44 | 34.66 |
| (±)IMM-H014 | 10 | 0.843 ± 10.050## | 92.09 | 18.74 |
| Bicyclol | 10 | 0.819 ± 0.099# | 89.47 | 15.36 |

**P < 0.01, in comparison to the blank control group;
#P < 0.05,
P < 0.01, in comparison to the model group.

Pharmacokinetic Experiments

Experimental Example 5

1. Experimental Purposes

Male SD rats were intragastrically administrated with the single enantiomer and racemate of IMM-H014, to compare their pharmacokinetic characteristics in rat bodies.

2. Experimental Apparatus and Materials 2.1 Experimental Apparatus

An Agilent 6470 triple tandem quadrupole LC-MS meter (Agilent Technologies Inc.), a Mettler AG135-model electronic analytical balance, a pipette gun, a TDL-5-A centrifuge, a SIGMA mini-centrifuge, a nitrogen blower, and an animal weighing scale.

2.2 Experimental Materials (+)IMM-H014, (−)IMM-H014, (±)IMM-H014; methanol (MS Grade, a product of Fisher Scientific Inc., cat #179097); acetonitrile (MS Grade, a product of Fisher Scientific Inc., cat #177802); deionized water (Hangzhou Wahaha Co.); formic acid (HPLC Grade, ROE SCIENTIFIC INC, cat #6F2941); ethyl acetate (MS Grade, a product of Fisher Scientific Inc., cat #166828); 1.5 ml EP tubes.

2.3 Experimental Animals 36 male SD rats (200±10 g), purchased from Beijing Vital River Laboratory Animal Technology Co., Ltd. The rats were raised in a clean room of an animal house in Institute of Materia Medica Chinese Academy of Medical Science, with light illumination for 12 hours every day at a temperature of 23±2° C. and in a relative humidity of 55±5%. The experimental animals could freely drink water and eat, and after 2-week acclimatization, the experiment was started. The research complies with the regulations made by Animal Experiment Ethics Committee of Institute of Materia Medica Chinese Academy of Medical Science.

3. Animal Experiments 3.1 Grouping and administrations of animals 36 male SD rats were randomly divided into 6 groups, 6 animals in each group, including: (+)IMM-H014 intragastric administration group, (−)IMM-H014 intragastric administration group, and (±)IMM-H014 intragastric administration group. The administration dosage was 50 mg/kg. The rats were in fasting for 12 hours before the administrations and they could freely drink water.

3.2 Preparation of Administration Solutions 100 mg of the IMM-H014 raw material drug was weighed and dissolved in 20 ml of purified water to prepare a 5 mg/ml administration solution, which was administrated (1 ml/100 g) in a single dose according to body weights.

3.3 Collection of Plasma Samples

At 0 hour before administrations, and at 5 min, 10 min, 30 min, 1 h, 2 h, 3 h, 5 h, 8 h, 12 h and 24 h after administrations, 250 μL of blood was taken from fundus plexus venosus, placed in an EP tube containing 10 μL of heparin sodium, and centrifuged at 4000 rpm for 10 min, and then the blood plasma was taken and stored in a refrigerator at −80° C.

4. Analytical Method 4.1 Solution Preparation 4.1.1 Preparation of Stock Solutions 5 mg of an IMM-H014 control sample was weighed precisely and placed in a 5 ml volumetric flask, and it was dissolved and diluted to the degree scale with methanol, to prepare a 1.0 mg/ml control stock solution.

4.1.2 Preparation of Internal Standard Working Solutions 5.0 mg of a Carbamazepine control sample was precisely weighed and placed in a 5 mL volumetric flask, and it was dissolved and controlled to the constant volume at the degree scale by adding methanol, to prepare an internal standard stock solution having a concentration of 1.0 mg/mL. 50 μL of the stock solution was precisely pipetted and placed in a 10 mL volumetric flask, and it was diluted and controlled to the constant volume at the degree scale by adding methanol, to prepare an internal standard concentrated stock solution with the concentration of 5.0 μg/mL. 5.0 mL of the internal standard concentrated stock solution was precisely pipetted and placed in a 50 mL volumetric flask, and it was diluted and controlled to the constant volume at the degree scale by adding methanol, to prepare an internal standard working solution with the concentration of 500 ng/m L.

4.1.3 Preparation of Standard Curve Working Solutions with a Series of Concentrations and Quality Control Standard Solutions 100 μL of a 1.0 mg/mL IMM-H014 stock solution was pipetted precisely and placed in a 10 mL volumetric flask, and it was diluted with methanol to prepare a solution of the IMM-H014 at 10 μg/mL. The solution was diluted stepwise with methanol to prepare IMM-H014 series standard solutions with the concentrations of 2, 5, 10, 50, 100, 500, 1000, 2000, 4000 and 5000 ng/ml.

A 1.0 mg/ml IMM-H014 stock solution was pipetted precisely and diluted stepwise with methanol to prepare quantity control standard solutions with the concentrations of 5, 100 and 4000 ng/ml.

4.1.4 Preparation of Matrix Standard Curve Samples and Quality Control Samples

50 μl of standard solutions at 2, 5, 10, 50, 100, 500, 1000, 2000, 4000 and 5000 ng/ml respectively were precisely pipetted and dried by blowing nitrogen gas at 30° C., and 50 μl of rat blank plasma was added thereto. After whirling the mixture for 3 min, matrix standard curve samples were prepared. 50 μl of standard solutions at 5, 100 and 4000 ng/ml respectively were precisely pipetted and dried by blowing nitrogen gas at 30° C., and 50 μl of rat blank plasma was added thereto. After whirling the mixture for 3 min, quality control samples were prepared.

4.2 Pretreatments of Samples

50 μL of a plasma sample was precisely pipetted, and after 10 μL of an internal standard working solution was added thereto, they were placed in a 1.5 ml EP. They were whirled for 30 s and added with 500 μl of ethyl acetate. Then, they were whirled and vibrated for 5 min, and after being kept still for 10 min at 4° C., they were centrifuged for 5 min at 13000 r. The supernatant was taken and dried by blowing $N_2$ at 30° C. The residue was re-dissolved by adding 100 μL of the initial mobile phase and centrifuged for 5 min at 13000 r, and the supernatant was transferred into a sampling bottle for measurements.

4.3 Chromatographic Conditions

Chromatographic column: Agilent ZORBAX SB-C18 (2.1×100 mm, 3.5 μm)

Mobile phase A: water (0.1% formic acid, 1 mM ammonium acetate); mobile phase B: acetonitrile (0.1% formic acid)

Column temperature: at 35° C.; sampling amount: 3 μL

Elution: 0-2 min: 40%-53% of the B; 2-3 min: 53%-40% of the B 4.4 Mass Spectrometry Conditions Ion source: ESI; detection mode: positive ions; temperature of drying gases: 300° C.; flow rate of drying gases: nitrogen gas, 11 L/min; atomizing gas: nitrogen, psi; capillary voltage: 4000 V; scanning mode: Multiple Reaction Measurement (MRM); ion pairs and related voltage parameters were shown below:

| Compound | Pre-ion (m/z) | Pro-ion (m/z) | CE (eV) | Fragmentor (V) | Polarity |
|---|---|---|---|---|---|
| IMM-H014 | 460.2 | 373.1 | 17 | 135 | Positive |
| IMM-H014 | 460.2 | 343.1 | 17 | 135 | Positive |
| Carbamazepine | 237 | 194 | 18 | 120 | Positive |

5. Data Processing

The original data obtained after samples were collected was treated by adopting MassHunter QQQ data processing software, to obtain blood-drug concentration data; then, the pharmacokinetic parameters were calculated through DAS software; finally, the t-test was performed by adopting SPSS software, to compare if there were statistical differences in drugs having the same optical activity but in different batches and in drugs having different optical activities, wherein the P<0.05 was considered to have significant differences. In the study, by intragastrically administrating 3 groups of SD rats with the single enantiomer and racemate of the IMM-H014 respectively, their pharmacokinetic characteristics in the rat bodies were studied. The results of the study suggested that the in vivo exposure levels of the intragastrically administrated (−)IMM-H014 and (±)IMM-H014 were superior to that of the (+)IMM-H014.

TABLE 8

Average pharmacokinetic parameters (excluding outliers) for each group of rats

| Parameter(s) | Unit | (+)-IMM-H014 | (−)-IMM-H014 | (±)IMM-H014 |
|---|---|---|---|---|
| AUC (0-t) | μg/L*h | 2876 ± 1978* | 5866 ± 2979 | 5242 ± 3447 |
| AUC (0-∞) | μg/L*h | 2877 ± 1977* | 5892 ± 3005 | 5268 ± 3432 |
| t1/2z | h | 0.984 ± 0.26 | 1.248 ± 0.33 | 1.206 ± 0.27 |
| Tmax | h | 0.334 ± 0.19 | 0.30 ± 0.18 | 0.209 ± 0.15 |
| CLz/F | L/h/kg | 25.0 ± 15.7 | 10.7 ± 6.2 | 14.0 ± 9.3 |
| Cmax | μg/L | 2277 ± 2001 | 3280 ± 1579 | 3324 ± 2307 |

*(+)-IMM-H014, in comparison to racemic IMM-H014, P < 0.05

The invention claimed is:

1. A left-handed bicyclic morpholine and a pharmaceutically acceptable salt thereof, characterized in that the structure of the left-handed bicyclic morpholine is shown by Compound 5, and the pharmaceutically acceptable salt has a structural formula (I):

5

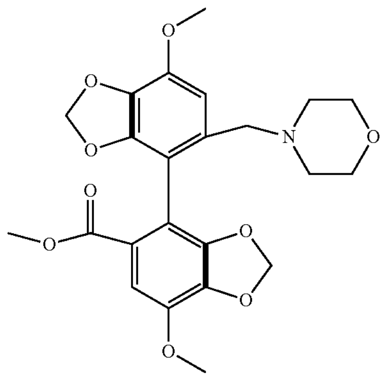

-continued

I

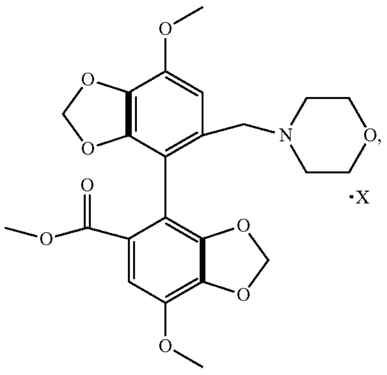

wherein X is selected from inorganic acids and organic acids.

2. The left-handed bicyclic morpholine and the pharmaceutically acceptable salt thereof according to claim 1, wherein: the inorganic acids are selected from hydrofluoric acid, hydrochloric acid, hydrobromic acid, hydroiodic acid, acetic acid, sulfuric acid, and phosphoric acid; the organic acids are selected from acetic acid, trifluoroacetic acid, propionic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, quinic acid, camphoric acid, camphorsulfonic acid, aspartic acid, glutamic acid, and pyroglutamic acid.

3. The left-handed bicyclic morpholine and the pharmaceutically acceptable salt thereof according to claim 1, characterized in that: the organic acids are selected from L-tartaric acid, L-dibenzoyl tartaric acid, L-di-p-methylbenzoyl tartaric acid, L-diethyl tartrate, L-malic acid, L-camphoric acid, L-10-camphorsulfonic acid, R-(−)-mandelic acid, L-quinic acid, L-aspartic acid, L-glutamic acid, L-pyroglutamic acid, D-tartaric acid, D-dibenzoyl tartaric acid, D-di-p-methylbenzoyl tartaric acid, D-diethyl tartrate, D-malic acid, D-camphoric acid, D-10-camphorsulfonic acid, S-(−)-mandelic acid, D-quinic acid, D-aspartic acid, D-glutamic acid, and D-pyroglutamic acid.

4. The left-handed bicyclic morpholine and the pharmaceutically acceptable salt thereof according to claim 1, characterized in that the pharmaceutically acceptable salt is selected from (−)-bicyclic morpholine methanesulfonate, having the following structure:

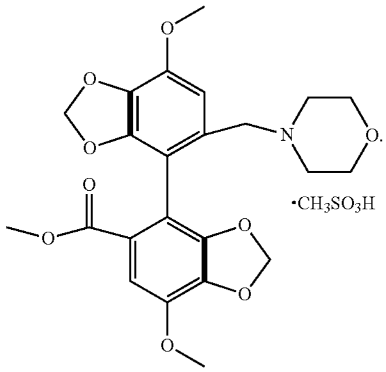

5. A process of preparing the left-handed bicyclic morpholine and the pharmaceutically acceptable salt thereof according to claim 1, characterized in that it comprises the following steps:

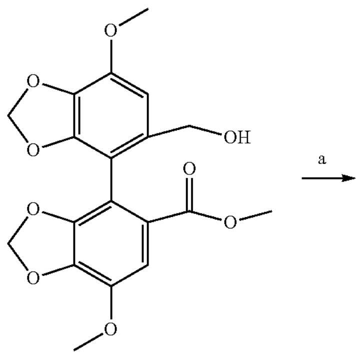

1

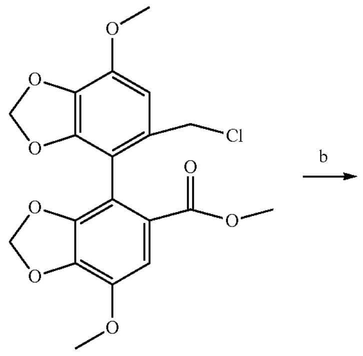

2

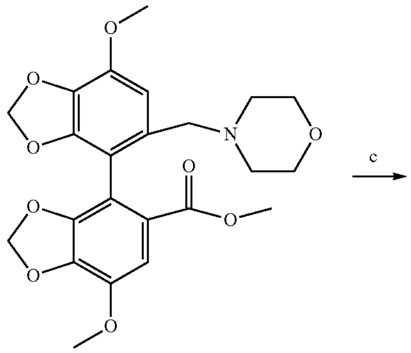

3

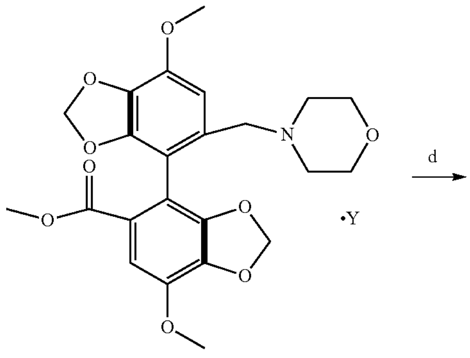

4

-continued

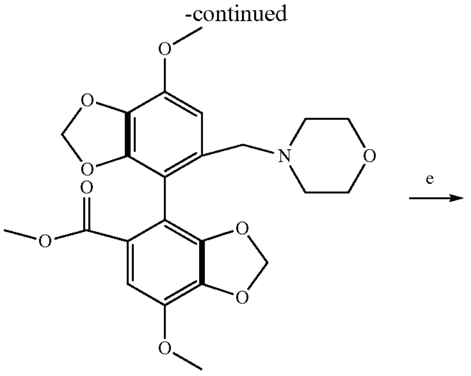

5

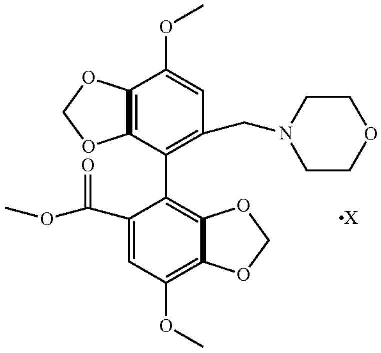

I a) chlorinating a hydroxy group of Bicyclol to obtain a compound 2; b) reacting the compound 2 with a morpholine to obtain a compound 3; c) forming a salt by reacting the compound 3 with a chiral acid Y, and performing resolutions in an organic solvent by utilizing the difference of salt solubility to obtain a levo salt 4, wherein the chiral acid Y is selected from L-tartaric acid, L-dibenzoyl tartaric acid, L-di-p-methylbenzoyl tartartic acid, L-diethyl tartrate, L-malic acid, L-camphoric acid, L-10-camphorsulfonic acid, R-(-)-mandelic acid, L-quinic acid, L-aspartic acid, L-glutamic acid, L-pyroglutamic acid, D-tartaric acid, D-dibenzoyl tartaric acid, D-di-p-methylbenzoyl tartaric acid, D-diethyl tartrate, D-malic acid, D-camphoric acid, D-10-camphorsulfonic acid, S-(-)-mandelic acid, D-quinic acid, D-aspartic acid, D-glutamic acid, D-pyroglutamic acid; the organic solvent is selected from ethyl acetate, acetone, methanol, ethanol, and isopropanol and solvents obtained by mixing the above solvents in different ratios; the % e.e. values of a levo enantiomer and a dextro enantiomer are respectively greater than 95%; d) enabling the salt 4 to be a free amine under the action of a base; e) optionally, forming a salt by reacting the free amine 5 with an acid X, to obtain the compound of formula I;

wherein X is selected from inorganic acids and organic acids.

6. A pharmaceutical composition, characterized in that it comprises the left-handed bicyclic morpholine and the pharmaceutically acceptable salt thereof according to claim 1, and optionally one or more pharmaceutically acceptable carriers or excipients.

7. A method for treating liver-related diseases in a subject, comprising administering the left-handed bicyclic morpholine and the pharmaceutically acceptable salt thereof according to claim 1 to the subject in need thereof.

8. The method according to claim 7, characterized in that the liver-related diseases are selected from liver injury-related diseases and hepatitis-related diseases.

9. The method according to claim 7, characterized in that the liver-related diseases are selected from hepatitis A, hepatitis B, hepatitis C, drug-induced liver diseases, alcoholic liver diseases, non-alcoholic liver diseases, autoimmune liver diseases, hepatic fibrosis induced by liver disease progression, liver cirrhosis, and liver failures.

10. A pharmaceutical composition, characterized in that it comprises the left-handed bicyclic morpholine and the pharmaceutically acceptable salt thereof according to claim 2, and optionally one or more pharmaceutically acceptable carriers or excipients.

11. A pharmaceutical composition, characterized in that it comprises the left-handed bicyclic morpholine and the pharmaceutically acceptable salt thereof according to claim 3, and optionally one or more pharmaceutically acceptable carriers or excipients.

12. A pharmaceutical composition, characterized in that it comprises the left-handed bicyclic morpholine and the pharmaceutically acceptable salt thereof according to claim 4, and optionally one or more pharmaceutically acceptable carriers or excipients.

13. A method for treating liver-related diseases in a subject, comprising administering the left-handed bicyclic morpholine and the pharmaceutically acceptable salt thereof according to claim 4 to the subject in need thereof.

14. The method according to claim 13, characterized in that the liver-related diseases are selected from liver injury-related diseases and hepatitis-related diseases.

15. The method according to claim 13, characterized in that the liver-related diseases are selected from hepatitis A, hepatitis B, hepatitis C, drug-induced liver diseases, alcoholic liver diseases, non-alcoholic liver diseases, autoimmune liver diseases, hepatic fibrosis induced by liver disease progression, liver cirrhosis, and liver failures.

* * * * *